United States Patent [19]

Bekanich

[11] Patent Number: 4,725,027

[45] Date of Patent: Feb. 16, 1988

[54] INTRAVENOUS EQUIPMENT SUPPORT

[76] Inventor: Joseph Bekanich, 483 N. Main St., Apt. A, Wilkes-Barre, Pa. 18705

[21] Appl. No.: 910,638

[22] Filed: Sep. 23, 1986

[51] Int. Cl.⁴ .............................................. F16M 1/04
[52] U.S. Cl. .................................... 248/125; 248/129; 248/542; 248/311.3; 248/408; 403/328; 403/361; 403/286
[58] Field of Search ...................... 248/125, 161, 295.1, 248/414, 129, 165, 542, 122, 311.3, 408, 544; 403/378, 328, 324, 361, 287, 13, 14; 211/205; D24/31; 604/80, 245, 246

[56] References Cited

U.S. PATENT DOCUMENTS

| 589,806 | 9/1897 | Bard | 248/165 X |
| 2,117,947 | 5/1938 | de Rome et al. | 403/324 X |
| 2,957,187 | 10/1960 | Raia | 248/161 X |
| 3,390,897 | 7/1968 | Moore | 403/287 X |
| 3,864,048 | 2/1975 | Parker | 403/13 X |
| 4,332,378 | 6/1982 | Pryor | 248/188.7 X |
| 4,344,718 | 8/1982 | Taylor | 403/287 |
| 4,602,890 | 7/1986 | Duda | 403/328 X |

FOREIGN PATENT DOCUMENTS

| 0180691 | 5/1986 | European Pat. Off. | 403/287 |
| 424412 | 2/1935 | United Kingdom | 403/324 |

Primary Examiner—Ramon S. Britts
Assistant Examiner—Karen J. Chotkowski
Attorney, Agent, or Firm—Shoemaker and Mattare, Ltd.

[57] ABSTRACT

A telescopically adjustable intravenous equipment support pole can be selectively carried on a wheeled base, a wheelchair, or other wheeled patient transport device. An intermediate pole section carries a lower end fitting which cammingly engages a spring-urged non-rotatable radial latch pin on the lower pole section to enable positive releasable locking of the intermediate pole section to the lower pole section with the latter disposed on a wheeled base, wheelchair or other patient transport device.

4 Claims, 8 Drawing Figures

U.S. Patent  Feb. 16, 1988  4,725,027
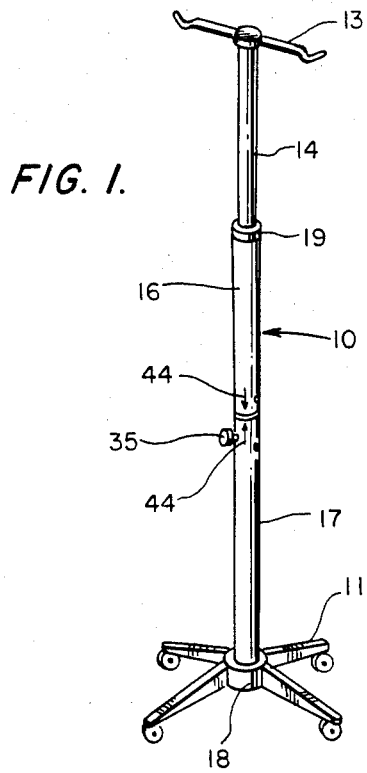
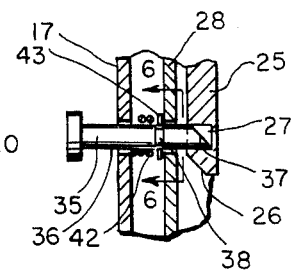
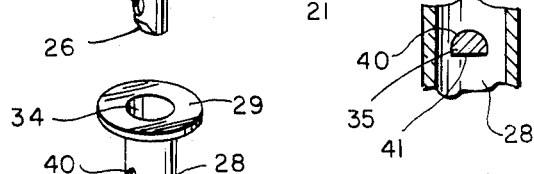
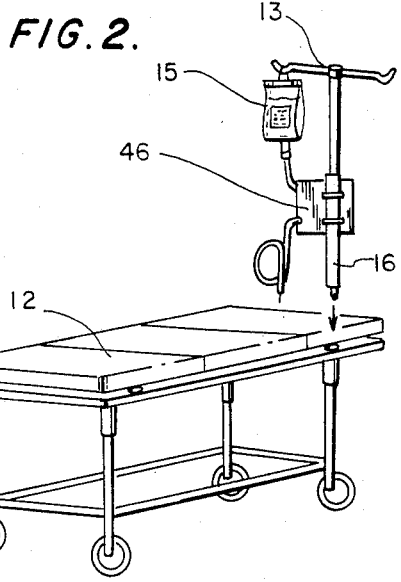
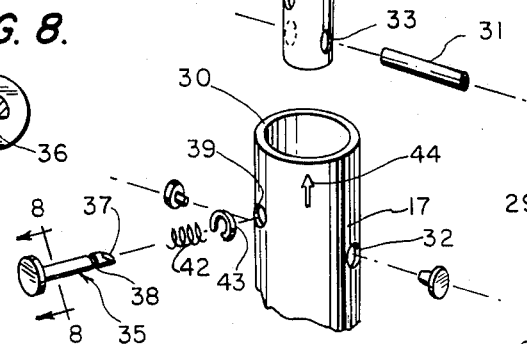
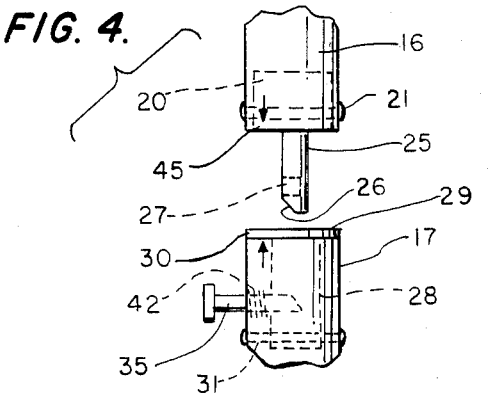

INTRAVENOUS EQUIPMENT SUPPORT

BACKGROUND OF THE INVENTION

1. Technical Field

The present invention relates to intravenous equipment transport devices and more particularly relates to a telescopically adjustable transport pole for intravenous equipment which may be locked conveniently and releasably to a wheeled base, a wheelchair or another patient transport unit.

2. Description of the Prior Art

The prior art transport devices for intravenous equipment have tended to be somewhat awkward and unstable and have also lacked convenience of usage. The common type one-piece intravenous equipment wheeled support pole has proven to be unstable and quite inadequate for propelling intravenous equipment through hospital corridors alongside a wheelchair. Prior art devices are known for connecting an intravenous support pole to a wheelchair or hospital stretcher and examples of such devices are shown in U.S. Pat. Nos. 3,709,556; 4,113,122; and 4,511,157.

An object of the present invention is, therefore, to provide an intravenous equipment support unit which is more simplified and more convenient to use and which can be releasably locked in a safe and secure manner to a hospital wheelchair or stretcher, or can optionally be provided with a stable wheeled base.

A further object of the invention is to provide an intravenous equipment support pole which is telescopically adjustable, and which includes a simple and efficient semi-automatic locking device whereby upper sections of the support pole can be quickly locked releasably to a pole base section by a manual "plug-in" action, with the pole base section attached either to a wheeled base or a wheelchair or the like.

Other objects and advantages of the invention will become apparent to those skilled in the art during the course of the following detailed description.

SUMMARY OF THE INVENTION

The invention is best summarized as a telescopically adjustable pole or standard for intravenous equipment which may be attached to a wheelchair or other patient transport device, or may be provided with an independent stable wheeled base. A lock fitting on the lower end of one pole section coacts cammingly with a spring-urged non-rotatable lock pin on an underlying pole section, with the lock pin passing through a guide aperture formed in an intermediate sleeve which is seated on the underlying pole section and secured thereto against rotation. The arrangement enables a semi-automatic quick locking operation and a manual release operation.

BRIEF DESCRIPTION OF THE DRAWINGS

FIG. 1 is a perspective view of a mobile intravenous equipment support according to the present invention.

FIG. 2 is a perspective view of the support attached to a stretcher.

FIG. 3 is an exploded perspective view of a releasable locking means for adjacent sections of the support according to the present invention.

FIG. 4 is a fragmentary exploded side elevation of the releasable locking means.

FIG. 5 is an enlarged fragmentary vertical section through the engaged releasable locking means.

FIG. 6 fragmentary vertical section taken on line 6—6 of FIG. 5.

FIG. 7 is a fragmentary side elevation of a guide sleeve for the releasable locking pin.

FIG. 8 is an enlarged vertical section through the locking pin taken on line 8—8 of FIG. 3.

DETAILED DESCRIPTION

Referring to the drawings in detail wherein like numerals designate like parts, a pole or standard 10 for intravenous equipment can be used on a wheeled base 11 as shown in FIG. 1, or on a stretcher 12, FIG. 2, or other patient transport means. As shown in FIG. 2, a support bar 13 on the top section 14 of the pole 10 may support one or two intravenous containers 15 to meet a particular patient's needs. An infusion pump 46 can also be mounted preferably on the intermediate section 16 of the pole 10.

The pole 10 further includes a base section 17 which is secured to a hub 18 of the wheeled base 11, (FIG. 1) and can be utilized as an independent support unit or, if desired, the pole sections can be removed from the support hub and either pole section 10 or 17 can be attached to the frame of the stretcher 12 as shown in FIG. 2. The pole sections 16 and 17 are tubular, as best shown in FIG. 3. The top section 14 can be tubular or solid, as desired. The top section 14 telescopes into the intermediate pole section 16 and is height-adjustable and may be locked in selected adjusted positions by a clamp device 19.

In accordance with the essence of the present invention, a fitting sleeve 20 is received telescopically in the bottom end of pole section 16 and is fixed therein rigidly by a cross pin 21 engaging through registering apertures 22 and 23 of the pole section 16 and fitting sleeve 20. Rivets 24 may also be employed to plug the apertures 22 outwardly of the pin 21, or rivets can be used in lieu of the pin 21, if desired, for joining the fitting sleeve 20 and pole section 16 rigidly.

A shaft extension 25 fixed centrally to the bottom end of fitting sleeve 20 has a lower end inclined camming face 26 and a locking pin keeper recess 27 opening through its side above the camming face 26.

The top end of pole base section 17 receives concentrically therein a receiver sleeve 28 for the shaft extension 25 and has a flat head 29 attached thereto which is seated on the top end face 30 of pole base section 17. The receiver sleeve 28 is fixed concentrically within the post section 17 by a cross pin 31 received through registering apertures 32 and 33 of the post section 17 and receiver sleeve 28.

The shaft extension 25 preferably has a close sliding fit within the bore 34 of the receiver sleeve 28. The lower end of the fitting sleeve 20 is flush with the lower end of the pole section 16.

A radial lock pin 35 has a flat longitudinal surface 36 on one side thereof and is provided with a leading end angled flat camming face 37 and an annular groove 38 somewhat rearwardly of the camming face 37. The lock pin 35 is received through a radial opening 39 of the pole base section 17 and the pin further passes through an aligned opening 40 of the receiver sleeve 28 having a chord straight edge 41. The cross section of the pin 35 matches the shape of the opening 40 and therefore the opening 40 prevents rotation of the lock pin and keeps the angled camming face 37 properly aligned to engage the camming face 26 of shaft extension 25 when the latter descends into the bore of the receiver sleeve 28.

The lock pin 35 is biased inwardly toward engagement with the shaft extension 25 by a spring 42 surrounding the lock pin 35 with its outer end bearing on the wall of pole base section 17 and its inner end engaging a spring retainer ring 43 engaged in the groove 38 of lock pin 35.

In order to assure quick and convenient locking of the two pole sections 16 and 17 in assembled relationship in either environment shown in FIGS. 1 and 2, alignment indicator arrows 44 are provided on the opposing end portions of pole sections 16 and 17. These indicator arrows are arranged in longitudinal alignment when the shaft extension 25 is inserted into the receiver sleeve 28. This assures proper radial alignment of the lock pin keeper recess 27 with the lock pin 35. Also, when the lower end face 45, FIG. 4, of fitting sleeve 20 abuts the top face of flat head 29, the keeper recess 27 will be positioned in coaxial alignment with the locking pin 35 so that the latter will snap into the keeper recess 27 following passage of the camming face 26 across the camming face 37 of the lock pin 35. During such engagement of the two camming faces 26 and 37, the lock pin 35 will be cammed radially outwardly, compressing the biasing spring 42, and will then snap into the recess 27 under influence of the spring 42.

It is now apparent that the described construction allows the two pole sections 16 and 17 to be snap locked together with a quick and convenient "plug in" type of engagement once the indicator arrows 44 have been aligned. The releasable locking engagement is therefore semi-automatic. The two pole sections 16 and 17 are easily separated by manual retraction of the lock pin 35 from the keeper recess 27, followed by pulling the pole sections 16 and 17 apart axially.

The safety, convenience and quickness of operation of the invention should now be appreciated by those skilled in the patient care art.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. In a mobile intravenous equipment support,
an extensible and retractable post adapted to support intravenous equipment and including a base section and another section directly above the base section, said sections being tubular, said sections having alignment indicating markers thereon adjacent to opposing ends thereof,
a detachable fitting sleeve fixed within the lower end of said another section,
a shaft extension secured to the fitting sleeve centrally thereof and extending downwardly therefrom and having a lower end camming face and a radial keeper recess somewhat above the camming face,
a removable and replaceable receiver sleeve fixed concentrically within the top of the base section in coaxial alignment with the shaft extension and having a bore adapted to closely receive the shaft extension and having a radial opening including a chord straight edge for alignment purposes,
a radial lock pin engaged through a radial opening of the base section and having a chord flat longitudinal face for engagement with and alignment by said chord straight edge in said radial opening and an inner end camming face, and
yielding means biasing the lock pin radially inwardly whereby the lock pin will automatically enter the keeper recess of the shaft extension following engagement of said camming faces when the shaft extension is inserted into the receiver sleeve while said indicating marker are longitudinally aligned.

2. In a mobile intravenous equipment support as defined in claim 1, and said camming faces comprising flat faces disposed at substantially equal angles to the ends of said shaft extension and lock pin.

3. In a mobile intravenous equipment support as defined in claim 1, and said yielding means comprising a biasing spring connected between the radial lock pin and the base section.

4. In a mobile intravenous equipment support as defined in claim 1, and said detachable fitting replaceable sleeve and said receiver sleeve being pinned respectively to said another section and said base section of the post.

* * * * *